United States Patent [19]

Zeikus et al.

[11] 4,352,885

[45] Oct. 5, 1982

[54] PREPARATION OF A NOVEL NADP LINKED ALCOHOL-ALDEHYDE/KETONE OXIDOREDUCTASE FROM THERMOPHILIC ANAEROBIC BACTERIA FOR ANALYTICAL AND COMMERCIAL USE

[75] Inventors: Joseph G. Zeikus, Madison, Wis.; Raphael J. Lamed, Schenectady, N.Y.

[73] Assignee: Wisconsin Alumni Research Foundation, Madison, Wis.

[21] Appl. No.: 148,243

[22] Filed: May 9, 1980

[51] Int. Cl.$^3$ .................... C12N 9/02; C12N 9/04; C12Q 1/32

[52] U.S. Cl. .................... 435/189; 435/25; 435/26; 435/190; 435/814; 435/822; 435/842

[58] Field of Search ............ 435/189, 190, 822, 842, 435/221, 222, 25, 26, 814

[56] References Cited

U.S. PATENT DOCUMENTS

| | | | |
|---|---|---|---|
| 3,796,635 | 3/1974 | Delente | 435/221 |
| 4,131,727 | 12/1978 | Lange et al. | 435/190 X |
| 4,250,259 | 2/1981 | Hou et al. | 435/190 X |

OTHER PUBLICATIONS

Tsai et al., Archives Biochemistry and Biophysics, vol. 199, No. 2, pp. 626–634, 1980.
Hou et al., Applied and Environmental Microbiology, Jul. 1979, pp. 135–142, vol. 38, No. 1.
Patel et al., Eur. J. Biochem. 101, 401–406 (1979).
Barth et al., Zeitschrift fur Allgemeine Mikrobiologie, 19, 381–390 (1979).
Zeikus et al., Enzyme Microb. Technol., vol. 1, pp. 243–252 (Oct. 1979).

*Primary Examiner*—Lionel M. Shapiro
*Attorney, Agent, or Firm*—McDougall, Hersh & Scott

[57] ABSTRACT

A partially purified NADP specific thermostable alcohol, aldehyde/ketone oxidoreductase is prepared which can react with a wide range of alcohols, ketones and aldehydes. The enzyme has a unique preference for secondary over primary alcohols. The thermostability, broad range of operating temperatures and lack of sensitivity to metal ions and complexing agents, in addition to the absolute specifity for the coenzyme, increase the utility of the enzyme in asymmetric organic synthesis and NADPH regeneration.

6 Claims, 1 Drawing Figure

PREPARATION OF A NOVEL NADP LINKED ALCOHOL-ALDEHYDE/KETONE OXIDOREDUCTASE FROM THERMOPHILIC ANAEROBIC BACTERIA FOR ANALYTICAL AND COMMERCIAL USE

BACKGROUND OF THE INVENTION

This invention relates to NADP linked mixed-function alcohol, aldehyde/ketone oxidoreductases derived from thermophilic anaerobic bacteria and, particularly, to thermostable NADP specific enzymes, a method for producing such enzymes and uses thereof analytically and commercially.

Nicotinamide adenine dinucleotide phosphate (NADP) linked alcohol dehydrogenases have previously been detected in *L. mesentroides, C. thermosaccharolyticum* and *C. kluyeri.* Secondary alcohol dehydrogenase activity, often associated with ethanol dehydrogenases, is usually less in these bacteria than is primary alcohol dehydrogenase activity. Such alcohol dehydrogenases have a number of synthetic and diagnostic uses, but commercial preparations lack sufficient heat stability and are too substrate specific for general use.

The NADP specific thermostable alcohol aldehyde, ketone oxidoreductases of the present invention, however, can react at elevated temperatures with a wide range of alcohols, ketones and aldehydes. A unique preference for secondary over primary alcohols is observed according to the following decreasing order of activity: secondary alcohols, ketones and aldehydes, and primary alcohols.

It is an object of this invention to provide for the preparation and use of thermostable NADP linked enzymes from thermally stable microorganisms, such as *Thermoanaerobium brockii (T. brockii)* and *Clostridium thermohydrosulfuricum;* and, at least, the partial purification thereof for analytical and commercial use. Other species such as *C. thermocellum* do not have these enzymes.

The invention will hereinafter be described with respect to the preparation of NADP linked alcohol dehydrogenase or alcohol-aldehyde/ketone oxidoreductase using *T. brockii* and *C. thermohydrosufuricum* as representative of the thermostable microorganisms.

SUMMARY OF THE INVENTION

Thermophilic bacteria can be cultured on a variety of energy sources. Substrates catabolized by thermophiles include common biopolymers, sugars, polypeptides, amino acids, alcohols, carboxylic acids and hydrocarbons.

*T. brockii,* specifically, can grow in the presence of starch/glycogen, glucose, maltose, cellobiose, sucrose, lactose and pyruvate. *C. thermohydrosulfuricum,* on the other hand, in addition to the above, uses cellobiose, mannitol and pentoses, such as arabinose and xylose.

The present invention relates to a method for producing NADP specific alcohol aldehyde/ketone oxidoreductases or alcohol dehydrogenase from thermophilic anaerobic bacteria and the analytical and commercial uses of such enzymes.

The thermostable enzymes are prepared by inoculating a substrate enriched basal salt medium with a strain of thermophilic bacteria, incubating the bacterial cells at an elevated temperature, collecting the heat treated cells and separating from the mixture a cell extract which contains the thermostable enzymes.

Partial purification of the enzyme can be achieved by heating the extract at 90° C. for 5 minutes. Alternatively, the enzyme-containing cell extract can be partially separated from the thermophilic bacterial culture extract by chromatographic methods. The heat treated cell extract is applied to a diethylaminoethyl-cellulose (DEAE-cellulose) column followed by application to a blue-dextran-sepharose column.

The prepared enzymes are advantageous in a number of analytical and commercial applications. The utilization of thermophilic bacteria and thermostable enzymes has specific advantages, for example, in the commercial production of chiral alcohols. The operation of fermenters at temperatures compatible with thermophilic bacterial growth prevents the accumulation of non-thermophilic bacterial and viral pathogens.

In addition, at the elevated temperatures necessary for fermentation, thermophilic bacteria have high rates of metabolism. The coupling of a high metabolic rate with an increased temperature activity and stability suggests a less expensive method for temperature control in the heating and cooling of industrial-scale fermentation.

Thermophilic processes also have the advantage of allowing shorter retention times, higher loading rates and increased reactor volumes. These features are of particular importance in large volume processes such as industrial, municipal and agricultural waste disposal, and chemical feedstock and fuel production. Likewise, the low activity and high stability of thermophilic cells and enzymes at room temperature lessen the need for refrigeration during exo-enzyme or cell recovery, and a catalytic activity with a longer half-life is provided for the development of enzyme immobilization technology.

DETAILED DESCRIPTION OF THE INVENTION

Growth of Microorganisms

Figure 1:
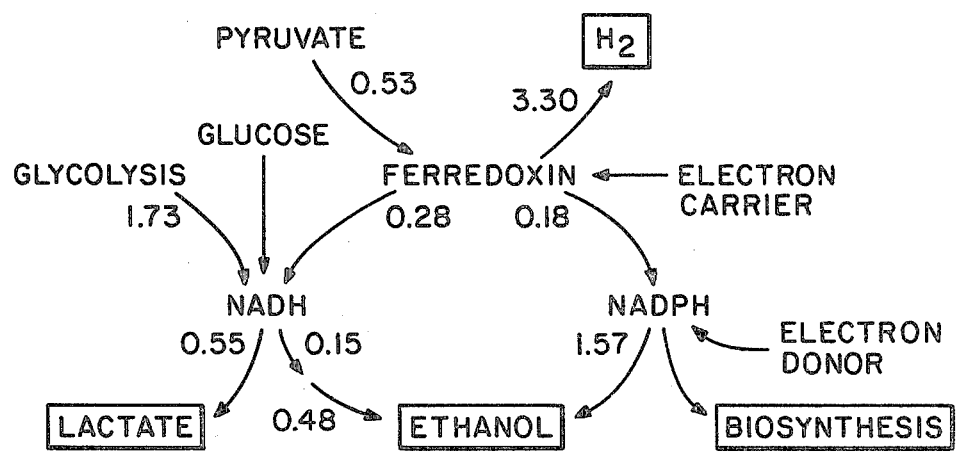

For the growth of the cells, use was made of *Thermoanaerobium brockii* Neotype Strain HTD-4 (ATCC 33075) and *Clostridium thermohydrosulfuricum,* Strain 39E (ATCC 33223) (American Type Culture Collection—Rockville, Md.).

Fermentation for cell growth was performed in a complex medium that contained 0.6% yeast extract, 1.0% tryptone, 1.0% glucose and 0.4% by weight acetone. The pH was maintained at about neutral and the solution was degassed with nitrogen.

The cells were cultured in anaerobic culture tubes containing 10 ml medium and were incubated at 60° C. without shaking. Thereafter, the cells were grown in 200 liter fermenters containing 200 liters of the same medium as described above. Fermenter cultures were maintained at neutral pH, with constant stirring at 100 rpm and continuous $N_2$ gassing (20 cc/min.), at 65° C. for *C. thermohydrosulfuricum* and *T. brockii.* Cells were harvested in their late exponential growth phase (optical density 500 nanometers greater than 2.0) by centrifugation at 35,000 G.

Preparation of Heat Treated Crude Extract

The centrifuged cells were suspended in several volumes of acetone, decanted, filtered and washed with additional acetone before drying to yield a dry enzyme preparation. 200 grams of the enzyme preparation was suspended in 25 mM Tris(hydroxymethyl) aminomethane.HCl (Tris-HCl) at pH 7.4, 2 mM dithiothreitol and 5 μg/ml DNAse. After stirring for 30 minutes, the suspension was diluted two-fold with water and heated at 90° C. for 5 minutes. Upon cooling, a heavy precipitate was formed. The supernatant obtained after centrifugation for 30 minutes at 20,000 G contained the crude heat treated enzyme.

In the alternative, the cell extract can be prepared as follows from a suspension of 2 g wet cells in 10 ml of 30 mM Tris-Cl at pH 7.3. The crude extract was diluted two-fold, heated for 5 minutes at 90° C. and centrifuged to remove the precipitate. The supernatant was then applied to a diethylaminoethyl cellulose (DEAE-cellulose) column and equilibrated at pH 7.3 with 50 mM Tris-Cl. Most of the active enzyme was eluted with the equilibrating buffer.

The fractions, containing the washed out activity, were combined and applied to a 2 ml blue-sepharose column (blue dextran-sepharose-4B, CL conjugate) which was equilibrated at pH 7.3 with 50 mM Tris-Cl. After washing, the activity was recovered by elution with 2 mM NADP in the same buffer. The overall purification was 44-fold, with a yield of about 70%; most of the loss occurred at the DEAE cellulose step.

Analysis by sodium dodecylsulfate (SDS) gel electrophoresis gave a major band of 37,000 daltons and a minor 33,000 dalton band. The preparation contained some NADPH oxidase which apparently was co-purified with the alcohol dehydrogenase. The DEAE-cellulose chromatography indicated that the primary and secondary alcohol dehydrogenase originated from the same protein.

The following table lists the specific activities measured at 40° C. of the *T. brockii* enzyme preparation with various alcohols and carbonyl compounds using NADP and NADPH as coenzymes at saturating levels of the substrates. A unit of enzyme activity represents the amount of enzyme necessary to catalyze the conversion of 1μ mole of substrate per minute into specific products.

TABLE I

Activities of Partially Purified Alcohol Dehydrogenase Expressed in Units of μ Mole/Min./Mg Protein

| | Substrate | Activity V/ mg.at 60° C. |
|---|---|---|
| Primary alcohols: | $CH_3OH$ | 0 |
| | $CH_3CH_2OH$ | 3.2 |
| | $CH_3CH_2CH_2OH$ | 3.6 |
| | $CH_3CH_2CH_2CH_2OH$ | 4.1 |
| | $CH_3CH_2CH_2CH_2CH_2OH$ | 0.9 |
| Branched primary alcohols: | $CH_3CH_2(CH_3)CH_2OH$ | 3.1 |
| | $CH_3CH_2CH_2(CH_3)CH_2OH$ | 3.0 |
| Secondary alcohols: | $CH_3CH(OH)CH_3$ | 59.0 |
| | $CH_3CH_2CH(OH)CH_3$ | 78.0 |
| | $CH_2=CHCH(OH)CH_2CH_3$ | 65.0 |
| | $CH_3CH(OH)CH_2CH(OH)CH_3$ | 2.6 |
| Cyclic secondary alcohol: | Cyclohexanol | 12.2 |
| Aldehyde: | $CH_3CHO$ | 7.8 |
| Linear ketones: | $CH_3COCH_3$ | 10.4 |
| | $CH_3COCH_2CH_3$ | 7.6 |
| | $CH_3COCH_2CH_2CH_3$ | 4.2 |
| | Methyl cyclopropyl ketone | 0.5 |
| Cyclic ketones: | Cyclopentanone | 6.0 |
| | Cyclohexanone | 6.2 |
| | 2-Cyclohexanone | 4.9 |
| | 2-Methyl Cyclohexanone | 6.0 |
| | 3-Methyl Cyclohexanone | 2.0 |
| | 4-Methyl Cyclohexanone | 0.5 |
| | Cycloheptanone | 3.0 |
| | Cyclooctanone | 0 |

TABLE I-continued

Activities of Partially Purified Alcohol Dehydrogenase Expressed in Units of μ Mole/Min./Mg Protein

| Substrate | Activity V/ mg.at 60° C. |
|---|---|
| 4 Norbornanone | 4.9 |

Each assay cuvette contained 1 ml of a solution comprising 0.1 M Tris-Cl at pH 7.8, 0.5 mM NADP or 0.2 mM NADPH and 0.2–0.5 M alcohol or ketone (or 10 mM acetaldehyde). The increase or decrease in absorbance at 334 nm was followed during incubation at 40° C.

No activity could be detected with NAD or NADH as coenzymes, L-lactic acid or glycerol did not react as substrates. The optimum pH was 7.8 in Tris-Cl buffers for acetaldehyde reduction; whereas the optimum pH range was 7.8–9.0 for the oxidation of sec-butanol. The apparent Michaelis constants, $K_M$, were 0.15 mM and approximately 0.5 mM for acetaldehyde and sec-butanol, respectively, and were in the micromolar range for NADP and NADPH. The apparent $K_M$ designates the substrate concentration which gives half-maximal reaction velocity.

*T. brockii* and *C. thermohydrosulfuricum* both ferment glucose and other saccharides to $H_2/CO_2$, acetic acid, lactic acid and ethanol. In the presence of acetone, isopropanol is a fermentation product. The catabolic electron flow schemes for the glycolytic metabolism of *T. brockii* are shown in FIG. 1. The numerical values represent the specific enzyme activities (as indicated by the direction of the arrow) in μ mole/min./mg protein at 40° C. The same pathways are used in *C. thermohydrosulfuricum*.

Activities of acetaldehyde dehydrogenase (CoA acetylating) were found in *C. thermohydrosulfuricum* extracts as well as for *T. brockii*. Spectrophotometric measurement of this activity for these species in both directions was possible since the alcohol dehydrogenase was not inhibited by NAD and was fully reversible.

Both a reversible NAD linked ethanol dehydrogenase and a reversible NADP linked alcohol dehydrogenase, however, were detected in *T. brockii* cell extracts. The NAD linked ethanol dehydrogenase, but not the NADP linked enzyme activity, was oxygen sensitive. Other thermophiles such as *C. thermocellum* do not contain any NADP alcohol linked dehydrogenase and the NAD linked alcohol dehydrogenase was inhibited by NAD and active only in direction of acetalydehyde reduction. It is not a reversible enzyme.

After heating for 80 minutes, the alcohol dehydrogenase was completely stable at 80° C. but began to lose activity at 86° C. and was inactive at 98° C. The addition of millimolar concentrations of ethylenediaminetetraacetic acid (EDTA) did not decrease thermostability. No loss of activity was observed in frozen cell extracts which were thawed several months after preparation.

Metal ions, complexing agents and thiol reagents had the following effects. There was no significant activation or inhibition by 1 mM concentrations of $MgCl_2$, $CaCl_2$, $CuCl_2$ or $ZnCl_2$. EDTA and 8-hydroxyquinoline (1–2 mM) did not significantly inhibit activity when incubated with the enzyme and sec-butanol for 15 min. in the presence or absence of NADP. 2 mM orthophenanthroline had a minimal inhibitory effect (15–20%) on the secondary alcohol dehydrogenase activity.

On the other hand, 0.05 mM parachloromercuricbenzoate (PCMB) reacted instantly with the enzyme. Complete reversal of the PCMB inhibition, however, could be achieved within a few minutes after the addition of 5 mM dithiothreitol (DTT). The addition of 1 mM $ZnSO_4$ was also necessary for complete reactivation. N-ethylmaleimide (NEM) also inactivated the enzyme, but only at a relatively high concentration (1 mM) and the inactivation was slow (15 min.). Each of the above studies were performed at 40° C.

A number of novel and effective uses can be made of the NADP linked alcohol, aldehyde/ketone dehydrogenases of this invention, such as the stereo-specific small and large scale organochemical oxidation/reduction of alcohols, ketones and aldehydes for use in organic synthesis. In addition, chiral compounds can be produced on a large scale for use in high resolution chromatography; NADPH can be efficiently regenerated at a low cost in enzymatic syntheses; and the present alcohol dehydrogenases can be used to analyze and separate alcohols, ketones and aldehydes, particularly in biological fluids and enzymes are thus suitable for analytical enzyme electrodes.

The enzyme preparation may also be used with catalytic amounts of NADP and a secondary alcohol or ketone as an electron donor or acceptor in the oxidation/reduction process. Representative uses are illustrated by the following examples.

EXAMPLE 1

Preparation of Chiral Alcohols

As illustrated in the following reaction diagram, an NADPH regenerating system can be initiated with isopropanol as the electron donor for the reduction of 2-pentanone.

LARGE SCALE PREPARATION OF OPTICALLY ACTIVE 2-PENTANOL WITH ALCOHOL DEHYDROGENASE FROM T. BROCKII

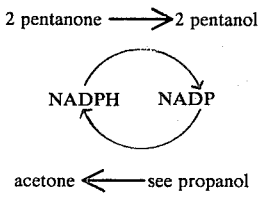

2 pentanone ⟶ 2 pentanol

NADPH   NADP acetone ⟵ see propanol

A 150 ml solution was prepared containing 50 mM Tris-HCl (pH 7.8), 0.2 v/v isopropanol, 2 mM dithiothreitol, 0.3 mM NADP and 3 g 2-pentanone. After the solution was degassed with $N_2$, sufficient heat treated *T. brockii* extract was added to yield an activity of 1 U/min./ml. The solution was incubated in a stoppered vessel for 40 hr. at 37° C. Gas chromatographic analysis indicated a 90% conversion of 2-pentanone to the corresponding alcohol. The mixture was extracted with diethyl ether and then fractionally distilled. The fractions were analyzed by conventional gas chromatographic and NMR (nuclear magnetic resonance) methods. The pure 2-pentanol fraction yielded a dextrorotatory optical rotation which corresponded to that of a highly optically enriched compound. The result in optical purity was dependent on incubation temperature and initial rate of isopropanol to 2-pentanone. Decreasing the temperature from 37° C. to 25° C. and the 2-pentanone concentration from 3 grams/150 ml to 0.6 grams/150 ml, increases the d/l bar ratio from 6/1 to 9/1 for the resulting 2-pentanol.

NADPH can also be regenerated on a larger scale, in which case a lower concentration of NADP can be used. A 2 liter solution was prepared that contained 0.05 NADP, 0.15 v/v isopropanol, and 0.1 v/v butanone. An excess of the butanone was converted to 2-butanol. In addition, incubation of the mixture at 45° C. or even 60° C. did not result in more than a 15% decrease in activity. Chiral (optically active) compounds can thus be produced on a large scale for use in, for example, high resolution chromatography.

EXAMPLE 2

Continuous Preparation of NADPH

The NADP linked alcohol dehydrogenase derived from *T. brockii* can be immobilized to continuously generate NADPH. A 10 ml mixture containing 120 units of the crude enzyme, 1 g powdered sepharose 4B-CnBr and 0.15 M sodium bicarbonate was prepared. After stirring the mixture for 4 hours at 4° C., 0.6 ml 1 M glycine was added and the resulting gelatinous suspension was stirred for an additional hour. The suspension was filtered and washed with 1 M sodium bicarbonate and 0.2 M Tris-HCl (pH 7.8). The filtrate showed no activity whereas the gel was active.

The gel was used to prepare a sepharose-alcohol dehydrogenase column (0.4×4.0 cm) which was then immersed in a water bath maintained at 45° C. A 0.01 M Tris-HCl solution (pH 9.0) containing 2.5 mg/ml NADP and 0.25 v/v isopropanol was applied to the column at a rate of 0.25 ml/min.; the treated solution was collected in a cooled ethanol precipitation vessel. Several milliliters of petroleum ether were added to 20 ml of the eluted solution and the precipitate was collected by centrifugation.

The reduction of NADP to NADPH was quantitative (as determined by ultraviolet absorption spectra). The recovered NADPH was identical to commercial samples and was effective in the assay of various NADPH requiring enzymes, such as: malate dehydrogenase (malic enzyme), glucose 6-phosphate dehydrogenase and the NADP linked alcohol dehydrogenase described herein.

EXAMPLE 3

The subject alcohol dehydrogenases may also be immobilized on an electrode for analytic use.

The immobilized alcohol dehydrogenase of example 2 was packed in a small flow cell which allowed amperometric measurement of NAPDH concentration, using a glossy carbon and Ag/Cl electrode with 0.8 volt potential difference. A soltuion containing 0.05 mM NADP and varying concentrations of sec. butanol 10–100 micro molar were passed through the cell and gave a signal which depended on the concentration of alcohol. Alternatively, solutions that contained 10 mM NADPH and varying concentrations of acetone produced signals which decreased linearly with increasing concentrations of acetone at 0–200 mM. Potassium phosphate buffer at 500 mM and pH 7.5 was used in these experiments. The immobilized enzyme system for measurement of ketones and alcohols was stable for 2 weeks at room temperature.

In this manner, a device for the continuous assay of NADPH, alcohols or carbonyl compounds is obtained that is sensitive to low concentrations of substrate.

EXAMPLE 4

Reduction of Ketones by *T. brockii* Cultures

*T. brockii* was incubated at 60° C. in anaerobic culture tubes containing the previously described TYEG medium supplemented with 0.5% acetone or butanone. More than 50% of each ketone was converted to the corresponding alcohol after 15 hours incubation. Growth of the organism ceased once the pH fell below 5.0. The reaction is indicated in FIG. 1 when acetone is substituted for glucose to produce the corresponding secondary isopropanol.

Similar results were obtained for 2-methyl cyclohexanone and *T. brockii* grown in an LPBM-0.3% yeast extract medium containing 0.5% glucose.

Additions of hydrogen in the growth vessel (0.03 atm.) increased the net conversion of ketone to secondary alcohols and was accompanied by a net conversion of hydrogen.

We claim:

1. A method for producing thermostable enzymes, said method comprising the steps of:
    (a) inoculating a culture medium with a strain of thermophilic bacteria selected from the group consisting of *Thermoanaerobium brockii* and *Clostridium thermohydrosulfuricum;*
    (b) incubating said bacteria at a temperature between 50° C. and 75° C.;
    (c) purifying the bacteria from spent culture supernatant fluids by heating to a temperature in the range of 85°–98° C.; and
    (d) isolating from the bacteria thermostable NADP linked alcohol, aldehyde/ketone oxidoreductases that are formed.

2. A method as claimed in claim 1 wherein the thermostable enzymes are isolated by centrifugation.

3. A method in accordance with claim 1 wherein said thermostable enzymes are isolated by applying said incubated bacteria to a chromatographic adsorbant selected from the group consisting of diethylaminoethyl cellulose, blue dextran-sephadex and sephadex.

4. A method as claimed in claim 1 in which the purification step is carried out by heating to a temperature within the range of 80°–98° C. for a time ranging inversely from 1–10 minutes.

5. A method as claimed in claim 4 in which the heat treatment is for a time of about 5 minutes at 90° C. to 10 minutes at 85° C.

6. A thermostable enzyme as claimed in claim 1 comprising an NADP linked alcohol dehydrogenase derived from a strain of thermophilic bacteria selected from the group consisting of *Thermoanaerobium brockii* and *Clostridium thermohydrosulfuricum* said dehydrogenase being stable after heating for 80 minutes at 80° C.

* * * * *